United States Patent [19]
Cartaxo

[11] Patent Number: 5,817,117
[45] Date of Patent: Oct. 6, 1998

[54] SURGICAL INSTRUMENT IN THE FORM OF A SCALPEL AND GUIDE FOR MAKING PERFECTLY CIRCULAR INCISIONS

[75] Inventor: Sidney Bandeira Cartaxo, Rus Teosompo de Vdsconcelos, Brazil

[73] Assignee: ZP XXI International, Miami Beach, Fla.

[21] Appl. No.: 922,768

[22] Filed: Sep. 3, 1997

[51] Int. Cl.⁶ .................................................. A61B 17/32

[52] U.S. Cl. .............................. 606/167; 606/1; 606/186; 606/187; 606/171; 128/303 R; 604/173; 623/15

[58] Field of Search ...................................... 606/167, 801, 606/186, 187, 171; 604/173; 623/15; 128/303 R

[56] References Cited

U.S. PATENT DOCUMENTS

| | | | |
|---|---|---|---|
| 4,892,096 | 1/1990 | Nayayranan | 606/1 |
| 5,569,237 | 10/1996 | Beckenstein | 606/1 |
| 5,676,161 | 10/1997 | Breiner | 128/898 |

*Primary Examiner*—Michael Powell Buiz
*Assistant Examiner*—Vy Q. Bui
*Attorney, Agent, or Firm*—Schweitzer Cornman Gross & Bondell LLP

[57] ABSTRACT

A surgical apparatus for making perfectly circular incisions comprises a cylindrical post; a ring supported at the bottom of the post for engaging a surgical site to be incised; a guide mounted for rotation on the post, the guide adapted to be translated upwardly and downwardly along the post; and a scalpel mounted on the guide, whereby the scalpel is adapted to incise a perfect circle on the surgical site.

3 Claims, 3 Drawing Sheets

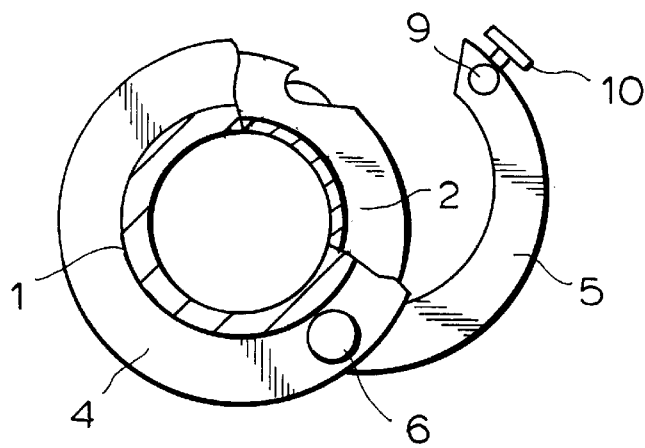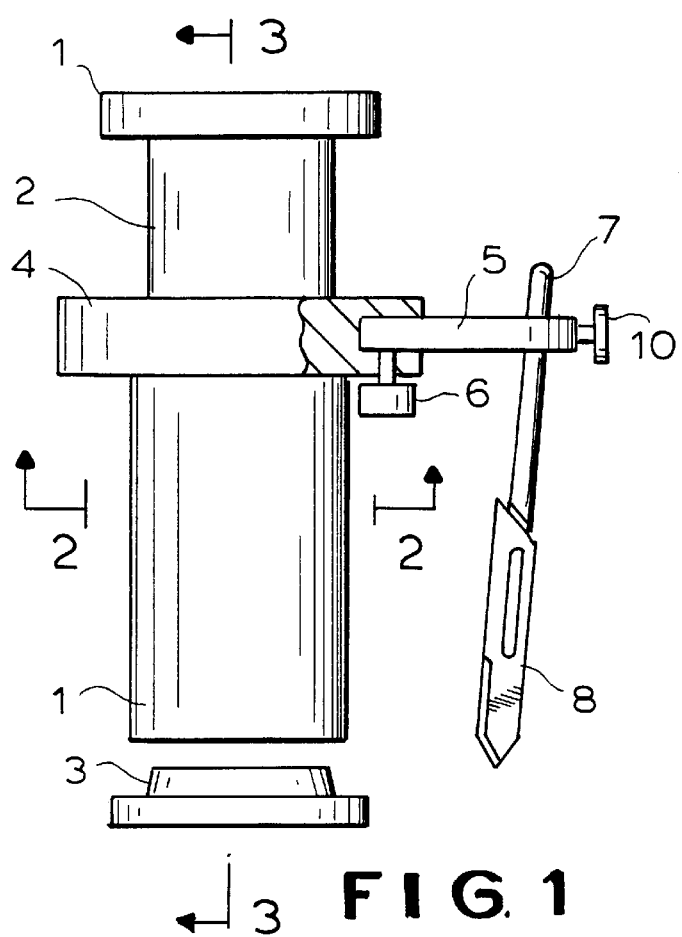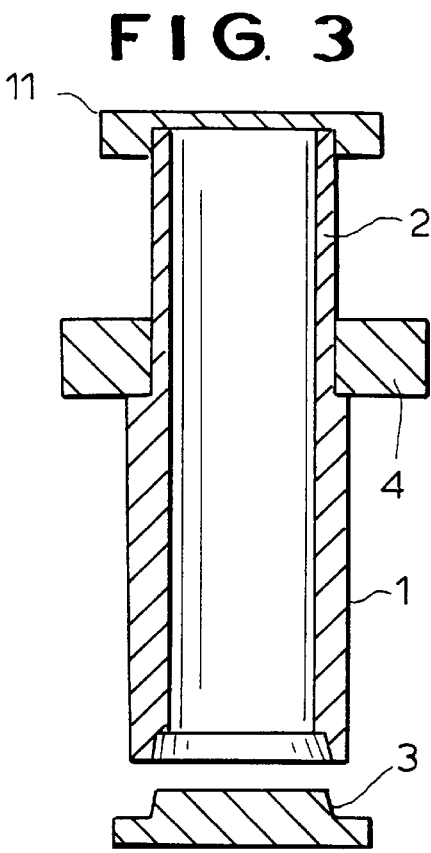

SURGICAL INSTRUMENT IN THE FORM OF A SCALPEL AND GUIDE FOR MAKING PERFECTLY CIRCULAR INCISIONS

BACKGROUND OF THE INVENTION

A significant portion of any breast surgery is dedicated to decorticating the mamillae for later reconstruction. Heretofore, this phase of the surgery has been done manually using an areola marker and a scalpel guided by the surgeon. This process takes a great amount of time during surgery and incurs risks that the incision will be irregular and not circular.

SUMMARY OF THE INVENTION

To overcome the shortcomings of performing purely manual "circular" incisions, the new and improved surgical tool of the present invention was developed to assist surgeons in performing perfectly circular incisions, particularly in the aesthetic surgery of the mammae.

The new instrument increases performance during the surgical process by allowing perfect and identical circular incisions. Its use decreases surgical time and reduces the hazard of tissue damage.

This new precision tool can reduce surgery costs since it requires a shorter period of anesthesia. Patients benefit by reduced post-anesthesia side effects and experience a lower risk of aesthetic scars.

DESCRIPTION OF THE DRAWINGS

FIG. 1 is a front elevational view of a first embodiment of the apparatus of the invention;

FIG. 2 is a horizontal cross-sectional view taken along line 2—2 of FIG. 1;

Fig. 3 is a vertical cross-sectional view taken along line 3—3 of FIG. 1;

DETAILED DESCRIPTION OF THE INVENTION

Figure 5:
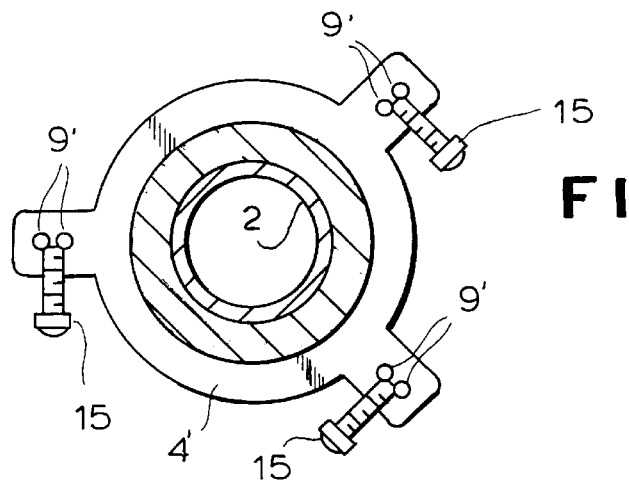
FIG. 5 is a horizontal cross-sectional view taken along line 5—5 of FIG. 4.

The apparatus of the invention illustrated in FIGS. 1, 2, and 3 is a first embodiment of the new scalpel and guide for making perfectly circular incisions. The apparatus includes a body having a hollow cylindrical body 1. The uppermost portion of body 1 forms a cylindrical guide post 2 which mounts a rotatable guide 4 thereon for rotational movement in a circular path about guide post 2. At the base of body 1 a removable circular base template ring 3, which contacts the surgical site to be incised, is positioned at the bottom of body 1. A series of base rings 3 in varying diameters is provided. A scalpel holder 5 is supported on the guide 4 by a threaded bolt 6. The holder 5 may be pivoted to adjust the radius of the circle to be incised by a scalpel 8 mounted on a rod handle 7 retained in a cylindrical angled opening 9 formed at the end of the holder 5. The rod handle 7 is secured within the opening 9 by a locking screw 10. A ring handle 11 is secured to top of guide post 2 for holding by a surgeon during cutting. The ring handle 11 ensures stability of the body portions 1,2 while the surgeon rotates guide 4 in a perfectly circular path about post 2 to form an incision.

Figure 6:
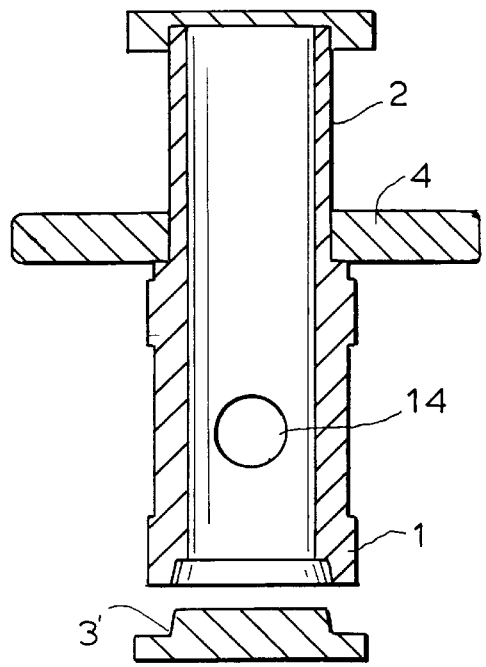
FIG. 6 is a vertical cross-sectional view taken along line 6—6 of FIG. 4.
Figure 4:
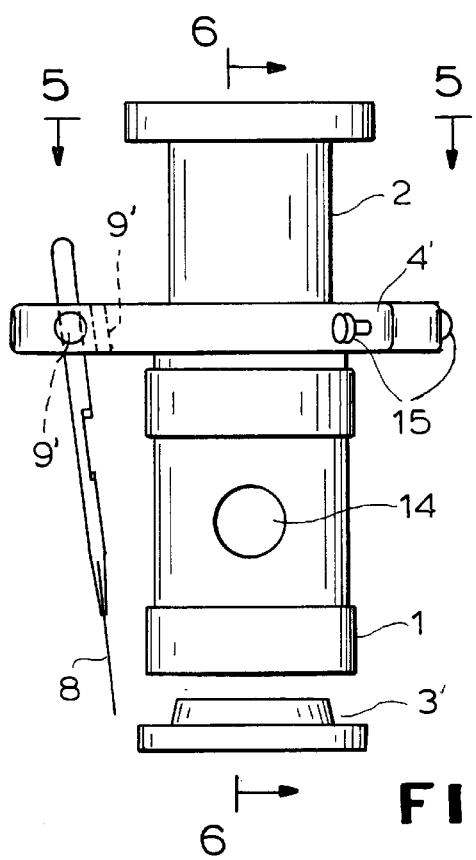
FIG. 4 is a front elevational view of a second embodiment of the apparatus of the invention.

FIGS. 4, 5, and 6 illustrate an alternative apparatus in which elements common to the apparatus of FIGS. 1–3 have common reference numerals, Advantageously, a tri-lobed scalpel guide 4' is employed in lieu of the scalpel guide 4. The guide 4' has six cylindrical openings 9', each drilled at a different angle to establish six different surgical cutting paths. Four viewing ports 14 are included in the body 1 to allow improved illumination of the center of the site to be cut. The rod handle 7 is secured to the guide 4' in one of the six openings 9'. Thereafter the rod is secured by a locking screw 15 which engages the openings 9', and the surgeon may perform a perfectly circular incision by rotating the guide 4' after the corresponding template ring 3' has been placed on the site to be cut.

Figure 7:
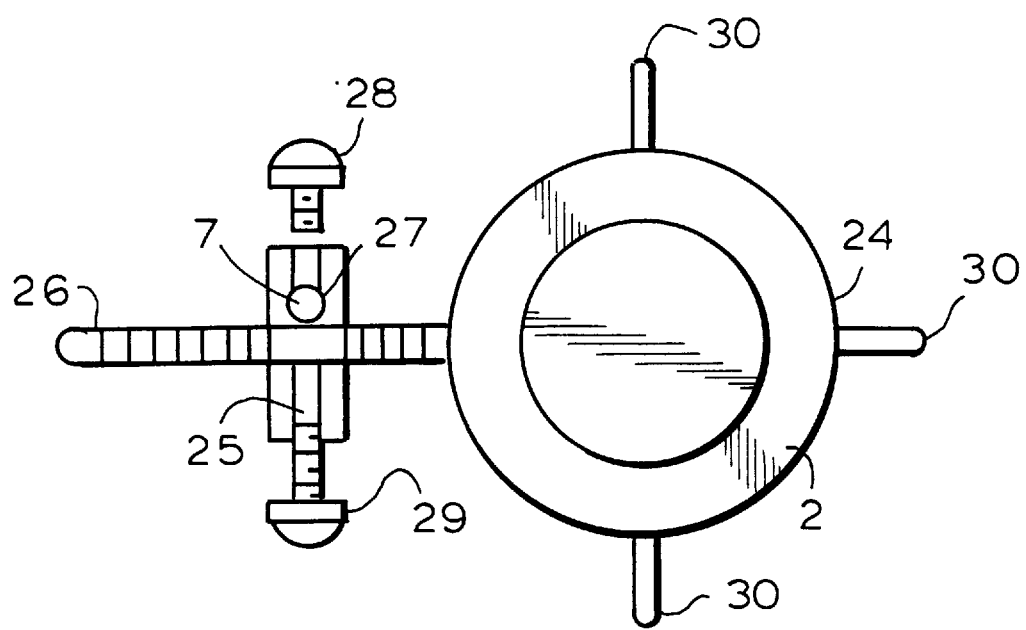
FIG. 7 is a plan elevational view of an alternative scalpel holder for use in the invention.

FIG. 7 shows yet another scalpel guide 24 for adjusting the radius of the scalpel from the center line of the apparatus. The scalpel guide 24 has grips 30 and is adapted to rotate about guide post 2 and to mount a scalpel handle 7 in a scalpel holder 25 which may be adjusted inwardly and outwardly on radially projecting stem 26. The scalpel handle 7 is locked in angled hole 27 by locking screw 28 while the holder 25 is locked to the stem 26 by locking screw 29.

Although the foregoing description has been given by way of preferred embodiments, it will be understood by those skilled in the art that other forms of the invention falling within the ambit of the following claims are contemplated. Accordingly, reference should be made to the following claims in determining the full scope of the invention.

I claim:

1. A surgical apparatus for making perfectly circular incisions, said apparatus comprising:
   (a) a cylindrical post means;
   (b) a ring means supported at the bottom of said post means for engaging a surgical site to be incised;
   (c) a guide means mounted for rotation on said post means;
   (d) said guide means adapted to be translated upwardly and downwardly along said post means;
   (e) a scalpel means mounted on said guide means;
   (f) whereby said scalpel means is adapted to incise a perfect circle on said surgical site.

2. The apparatus of claim 1 in which
   (a) said guide means includes a pivoting scalpel holder for adjusting the radius of the circle to be incised.

3. The apparatus of claim 1 in which
   (a) said guide means includes a radially displaceable scalpel holder for adjusting the radius of the circle to be incised.

* * * * *